United States Patent

Chang et al.

[11] Patent Number: 6,008,399
[45] Date of Patent: Dec. 28, 1999

[54] PROCESS FOR PREPARING ORGANIC CARBONATES

[75] Inventors: Clarence D. Chang, Princeton, N.J.; Jose G. Santiesteban, West Chester, Pa.

[73] Assignee: Mobil Oil Corporation, Fairfax, Va.

[21] Appl. No.: 09/266,623

[22] Filed: Mar. 11, 1999

[51] Int. Cl.$^6$ ............................................. C07C 68/00
[52] U.S. Cl. ...................... 558/277; 558/260; 558/274; 558/277
[58] Field of Search ...................... 558/274, 277

[56] References Cited

U.S. PATENT DOCUMENTS

| | | | |
|---|---|---|---|
| 3,114,762 | 12/1963 | Mador et al. | 260/463 |
| 3,139,440 | 6/1964 | Maggiolo | 558/277 X |
| 3,227,740 | 1/1966 | Fenton | 260/463 |
| 3,846,468 | 11/1974 | Perrotti et al. | 558/275 |
| 3,952,045 | 4/1976 | Gaenzler et al. | 558/275 |
| 3,980,690 | 9/1976 | Cipriani et al. | 558/277 |
| 4,131,521 | 12/1978 | Cipris et al. | 205/439 |
| 4,218,391 | 8/1980 | Romano et al. | 260/463 |
| 4,318,862 | 3/1982 | Romano et al. | 558/277 |
| 4,360,477 | 11/1982 | Hallgren et al. | 558/277 |
| 4,370,275 | 1/1983 | Stammann et al. | 558/277 |
| 4,429,331 | 1/1984 | Drent | 260/463 |
| 4,490,559 | 12/1984 | Wegman et al. | 568/484 |
| 4,625,044 | 11/1986 | Curnutt | 558/277 |
| 4,644,078 | 2/1987 | Morris et al. | 558/277 |
| 4,689,430 | 8/1987 | Morris et al. | 560/204 |
| 4,785,130 | 11/1988 | Bhattacharya | 558/277 |
| 5,004,827 | 4/1991 | Curnutt | 558/277 |
| 5,093,513 | 3/1992 | Sawicki et al. | 558/277 |
| 5,118,818 | 6/1992 | Delledanne et al. | 549/230 |
| 5,142,087 | 8/1992 | Joerg et al. | 558/277 |
| 5,183,920 | 2/1993 | Myers | 558/277 |
| 5,288,894 | 2/1994 | Landscheidt et al. | 558/277 |
| 5,387,708 | 2/1995 | Molzahn et al. | 558/277 |
| 5,391,803 | 2/1995 | King et al. | 558/277 |
| 5,414,104 | 5/1995 | Jentsch et al. | 558/277 |
| 5,478,962 | 12/1995 | De Nardo et al. | 558/277 |
| 5,523,452 | 6/1996 | Kricsfalussy et al. | 558/277 |
| 5,750,759 | 5/1998 | Hagen et al. | 558/277 |

*Primary Examiner*—Michael G. Ambrose
*Attorney, Agent, or Firm*—Malcolm D. Keen

[57] ABSTRACT

A process for preparing organic carbonates, such as dimethyl carbonate, without the use of phosgene and with a high yield and selectivity to the desired carbonate, by reacting a formaldehyde-acetal with a source of oxygen, in the presence of a catalyst.

10 Claims, No Drawings

PROCESS FOR PREPARING ORGANIC CARBONATES

This invention relates to a process for preparing organic carbonates. More specifically the present invention relates to a process for preparing dimethyl carbonate by reacting dimethoxymethane with a source of oxygen, in the presence of a catalyst.

BACKGROUND OF THE INVENTION

Organic carbonates are useful as intermediates in numerous chemical processes and as synthetic lubricants, solvents, plasticizers and monomers for organic glass and various polymers, including polycarbonate, a polymer known for its wide range of uses based upon its characteristics of transparency, shock resistance and processability.

One method for the production of polycarbonate resin employs phosgene and bisphenol-A as starting materials. However, this method has numerous drawbacks, including the production of corrosive by-products and safety concerns attributable to the use of the highly toxic phosgene. As such, polycarbonate manufacturers have developed non-phosgene methods for polycarbonate production, such as reacting dimethyl carbonate with bisphenol-A.

Dimethyl carbonate has a low toxicity and can be used to replace toxic intermediates, such as phosgene and dimethyl sulphate, in many reactions, such as the preparation of urethanes and isocyanates, the quaternization of amines and the methylation of phenol or naphthols. Moreover, it is not corrosive and it will not produce environmentally damaging by-products. Dimethyl carbonate is also a valuable commercial product finding utility as an organic solvent, an additive for fuels, and in the production of other alkyl and aryl carbonates.

Dimethyl carbonate, as well as other organic carbonates, have traditionally been produced by reacting alcohols with phosgene. These methods have the same problems as methods that use phosgene and bisphenol-A, i.e., the problems of handling phosgene and disposing of phosgene waste materials. Thus, there is a need for commercially viable non-phosgene methods for the production of dimethyl carbonate, as well as other organic carbonates.

Methods have been proposed for preparing dimethyl carbonate by the catalytic reaction of methanol with carbon monoxide and oxygen in accordance with the following equation:

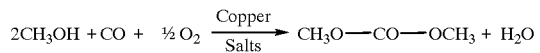

The copper compounds acting as catalysts in such a reaction are in the form of various copper salts. However, there are problems associated with using many of the proposed copper salts in an industrial process. For example, the use of copper(II) chloride as a catalyst gives unsatisfactory selectivities. Moreover, problems are caused by the formation of relatively large amounts of methyl chloride, which, because of its high volatility, is difficult to contain and can lead to corrosion in virtually the entire production plant.

Although the use of other catalyst salts in the form of organic complexing agents generally provides better selectivities than salts such as copper(II) chloride, such agents are typically only partially dissolved in the reaction mixture and the undissolved catalyst salts can cause processing problems. Specifically, the undissolved salts have to be conveyed through the reaction zone and cooling equipment and thereafter separated by mechanical means, such as a centrifuge. Such a method results in corrosion, poor heat transfer and blockages and encrustations associated with the undissolved salts.

One method that avoids the circulation of undissolved catalyst salts through the plant uses an excess of methanol. The process retains the suspended catalyst salts in the reactor and meters the methanol, carbon monoxide and oxygen feeds to the reactor, while removing dimethyl carbonate, water of reaction and methanol by distillation. However, the use of excess methanol results in a relatively low reaction rate and a low concentration of dimethyl carbonate. Additionally, since the reaction is carried out at high pressures and the solubilities of both dimethyl carbonate and water in the reaction medium are very high, it is difficult to separate the dimethyl carbonate and water.

Other methods for producing dialkyl carbonates, which utilize a homogeneous catalyst system, have been proposed. One method reacts an alcohol with carbon monoxide and oxygen in the presence of a catalyst system composed of complexes of metals which are capable, by oxy-reduction, of displaying two valency states. Although such methods may be satisfactory in producing alkyl carbonates, their use on an industrial scale has some drawbacks. Beyond the relatively high cost of complex catalyst systems, these systems have a low conversion of the alcohol because they are sensitive to the water and carbon dioxide formed together with the carbonate in the course of the reaction. There are difficulties, moreover, in the separation of the reaction products and more particularly of water and carbonate from the reactor effluent and from the homogeneous catalyst inasmuch as the ligand is normally an organic base and brings about a certain hydrolysis of the carbonate due to the water which is present in the system.

Methods have also been proposed for producing dialkyl carbonates by reacting an alkanol, carbon monoxide and oxygen in the presence of a catalyst which is heterogeneous to the reaction mixture, such as reacting the alkanol with carbon monoxide and oxygen in the vapor phase in the presence of a zeolite catalyst containing copper; reacting an alkanol, with carbon monoxide and oxygen in the vapor phase, in the presence of a catalyst containing: (1) a copper halide, a copper oxyhalide, or a copper carboxylate halide, (2) a quaternary ammonium salt, and (3) a support component; and reacting an alkanol with carbon monoxide and oxygen, in the vapor phase in the presence of a catalyst having a nitrogen-containing coordination compound copper hydrocarbyloxy halide complex supported on activated carbon.

Although such methods may be commercially viable, there still exists a need for economical methods for producing organic carbonates, such as dimethyl carbonate, on an industrial scale, due to the market potential for such products.

Other processes proposed for producing organic carbonates without the use of phosgene are the reaction of urea or urethanes with alcohols in the presence of catalysts, the reaction of alkyl halides or sulphates with alkaline carbonates, the reaction of carbon monoxide with alkyl nitrites in the presence of catalysts, the reaction of alcohols with carbon dioxide and electrochemical synthesis. However, these processes have little practical importance for producing organic carbonates on an industrial scale.

Thus, there is a need for an economical method of producing organic carbonates, such as dimethyl carbonate, on a commercial scale which does not have the above mentioned disadvantages.

SUMMARY OF THE INVENTION

According to the present invention, it has now been found that an organic carbonate, and more specifically dimethyl carbonate, can be prepared under mild conditions and with high yields, from a formaldehyde-acetal (dimethoxy methane in the case of dimethyl carbonate) and a source of oxygen, in the presence of a catalyst.

The present invention is a process for preparing an organic carbonate by reacting a formaldehyde-acetal with a source of oxygen in the presence of a catalyst.

Preferably, the organic carbonate of the present invention is of the formula:

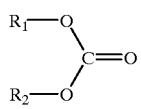
(I)

and the corresponding formaldehyde-acetal is of the formula:

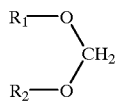
(II)

wherein: $R_1$ and $R_2$ independently of one another denote a $C_1$–$C_{10}$ linear or branched, substituted or unsubstituted, alkyl radical; a $C_5$–$C_8$ substituted or unsubstituted cycloalkyl radical; or a substituted or unsubstituted $C_6$–$C_{12}$ aryl radical.

In an embodiment of the present invention, dimethoxy methane is reacted with oxygen in the presence of a solid catalyst having a porous support or substrate and a metal component, to produce dimethyl carbonate.

In another embodiment, the invention provides for the selective co-production of dimethoxy methane in a secondary process. This secondary process involves reacting methanol with formaldehyde in the presence of a catalyst to produce dimethoxy methane. This dimethoxy methane may be selectively withdrawn as a product of the secondary process or may be used as a reactant in the process to produce dimethyl carbonate.

The present invention provides the advantage of producing organic carbonates, such as dimethyl carbonate economically, without the use of phosgene and with a relatively high yield and selectivity to the desired carbonate.

Additional objects, advantages and novel features of the invention will be set forth in part in the description and examples which follow, and in part will become apparent to those skilled in the art upon examination of the following, or may be learned by practice of the invention. The objects and advantages of the invention may be realized and attained by means of the instrumentalities and combinations particularly pointed out in the appended claims.

DETAILED DESCRIPTION OF PREFERRED EMBODIMENTS

The present invention is a process for preparing dialkyl and diaryl carbonates, as well as other organic carbonates, from a corresponding formaldehyde-acetal.

Preferably, in preparing, dialkyl and diaryl carbonates, the formaldehyde-acetal (II) is chosen from formaldehyde dimethyl acetal, formaldehyde diethyl acetal, formaldehyde di-n-propyl acetal, formaldehyde di-iso-propyl acetal, formaldehyde di-n-butyl acetal, formaldehyde di-iso-butyl acetal, formaldehyde di-2-ethyl-hexyl acetal, formaldehyde dicyclohexyl acetal, and formaldehyde diphenyl acetal, so that the $R_1$ and $R_2$ groups in formulas (I) and (II) are the same and represent a methyl, ethyl, n-propyl, iso-propyl, n-butyl, iso-butyl, 2-ethylhexyl, cyclo hexyl, and phenyl radical, respectively. The corresponding organic carbonate (I) preferably prepared is dimethyl carbonate, diethyl carbonate, di-n-propyl carbonate, di-iso-propyl carbonate, di-n-butyl carbonate, di-iso-butyl carbonate, di-2-ethyl hexyl carbonate, dicyclohexyl carbonate and diphenyl carbonate, respectively.

Other organic carbonates can also be prepared by the present invention where the $R_1$ and $R_2$ groups are different.

The reaction may be represented by the following:

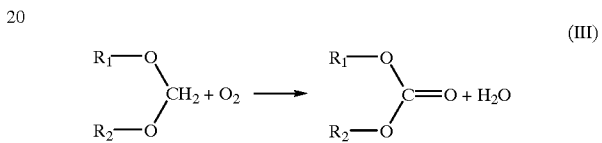
(III)

wherein $R_1$ and $R_2$ independently of one another denote a $C_1$–$C_{10}$ linear or branched, substituted or unsubstituted, alkyl radical; a $C_5$–$C_8$ substituted or unsubstituted cycloalkyl radical; or a substituted or unsubstituted $C_6$–$C_{12}$ aryl radical.

The source of oxygen (represented by $O_2$ in formula III) can be molecular oxygen ($O_2$), air, ozone, oxygenated organic compounds; oxygenated inorganic compounds; organic oxides, dioxides and peroxides; inorganic oxides, dioxides and peroxides; periodates; or mixtures thereof. The source of oxygen may be present under reaction conditions in gaseous or liquid form and may be in the presence or absence of an inert gas or liquid.

The source of oxygen can be an oxygen-containing gas (e.g., molecular $O_2$ or air) which is brought into contact with the formaldehyde-acetal reactant by conventional means, such as continuously bubbling the gas through the reaction mixture. The selection of the source of oxygen depends on the type of reactor and catalyst used, and is chosen to operate the process most economically. The content and amount of oxygen also depends upon reaction rate, reactor type and type of catalyst used, and is adjusted to maximize the economics of the process. Preferably, the amount of oxygen present under reaction conditions will be about the stoichiometric amount of oxygen or less determined by the balanced formula (III), to minimize side reactions.

The reactants (i.e., the formaldehyde-acetal and the source of oxygen) are contacted in the presence of a catalyst under reaction conditions. Preferably, the catalyst will be a solid catalyst containing an absorbent substrate or support structure with a metal component.

Absorbent substrates or supports which are useful in the method of this invention include porous, high surface area solids, such as activated carbon, inorganic ion-exchange materials, polymeric resins (both gel and macro-reticulous types), molecular seives, zeolites, silica, alumina, silica-alumina, silica-magnesia, aluminophosphate, silico alumina phosphate, metalloaluminophosphate, titania, zirconia, or mixtures or combinations thereof.

Specific examples of the inorganic ion exchange materials include both the naturally occurring materials such as the mineral zeolites including mordenite, clinoptilolite, erionite, sepiolite, clays and synthetic material, which include $Al_2O_3$, $SiO_2$, $SiO_2$—$Al_2O_3$, synthetic zeolites such as zeolite A, zeolite X, zeolite Y, ZSM-5 and mordenite.

Suitable zeolites for this invention also include aluminosilicate zeolites; typical members of this class are the zeolites having the structures of ZSM-5 (U.S. Pat. Nos. 3,702,886 and Re. 29,948); ZSM-11 (U.S. Pat. No. 3,709,979); ZSM-12 (U.S. Pat. No. 3,832,449); ZSM-22 (U.S. Pat. No. 4,556,477); ZSM-23 (U.S. Pat. No. 4,076,842); ZSM-35 (U.S. Pat. No. 4,016,245); ZSM-48 (U.S. Pat. No. 4,397,827); ZSM-57 (U.S. Pat. No. 4,046,685); ZSM-58 (U.S. Pat. No. 4,417,780); M-41S (U.S. Pat. No. 5,098,684) and MCM-22 (U.S. Pat. Nos. 4,954,325 and 4,962,256). Other isostructural forms of the zeolites containing other metals instead of aluminum such as gallium, boron or iron can also be used.

The catalyst can be shaped in the form of extrudates, cylinders, multi-lobes, pellets, granules, or be structure shaped (similar to the packing of static mixers).

The metal component of the solid catalyst can be a metal or combination of metals on the support alone or in the forms of metal oxides, metal sulfides, metal chlorides and spinels. Metal or metals of groups Ib, VIb and VIII of the Periodic Table (IUPAC Table, as shown, for example, in The Merck Index, Twelfth Ed.,1996) are generally useful in this process. The preferred metal or metals include copper, silver, iron, cobalt, nickel, ruthenium, palladium, platinum, molybdenum and tungsten. Combinations, such as Ni—Mo, Ni—W, Co—Mo, Cu—Pd and Ni—Co—Mo, are typical. The catalyst may be fresh or used commercial catalyst. The use of used catalyst may result in cost savings.

Commercial hydrotreating catalysts e.g., Ni—Mo/$Al_2O_3$, Mo/$Al_2O_3$, can be used, as can commercial hydrocracking catalysts, zeolites, or $SiO_2$/$Al_2O_3$ and reforming catalysts, e.g., Pt/$Al_2O_3$. If zeolites are employed, they can typically contain noble metals such as Pd or Pt, or metal combinations such as Ni—Mo, Ni—W, Cu—Pd or Co—Mo. Commercial hydrogenation catalysts, e.g., Pd/C, Ni/Kieselguhr, Pt/C, or Pt/$Al_2O_3$ can also be used in the process.

The catalyst is chosen to optimize the economics of the process, depending upon the source of oxygen used. For example, it is contemplated that copper-based catalysts, such as a copper oxide or copper chloride on an alumina ($Al_2O_3$), silica ($SiO_2$) or zeolite substrate, are particularly effective with oxygen or air. Redox complexes such as Cu—Pd are also effective.

It may also be useful to incorporate the above-described catalysts with a matrix of a material resistant to the temperature and other conditions employed in the process. Useful matrix materials include active and inactive materials and synthetic or naturally occurring zeolites as well as inorganic materials such as clays, silica and/or metal oxides. The latter may be either naturally occurring or in the form of gelatinous precipitates, sols or gels including mixtures of silica and metal oxides. Use of a material in conjunction with the above-described catalysts, i.e., combined therewith, which is active, may be useful in improving the conversion and/or selectivity of the catalyst. Inactive materials may suitably serve as diluents to control the amount of conversion and/or selectivity of the catalyst. Frequently, zeolite or other crystalline materials have been incorporated into naturally occurring clays, e.g., bentonite and kaolin. These materials, i.e., clays, oxides, etc., function, in part, as binders for the catalyst. It is desirable to provide a catalyst having good crush strength, because in practice the catalyst is often subjected to rough handling, which tends to break the catalyst down into powder-like materials which cause problems in processing.

Naturally occurring clays which can be composited with the above-described catalysts include the montmorillonite and kaolin family, which families include the sub-bentonites, and the kaolins commonly known as Dixie, McNamee, Georgia and Florida clays or others in which the main mineral constituents is halloysite, kaolinite, dickite, nacrite, or anauxite. Such clays can be used in the raw state as originally mined or initially subjected to calcination, acid treatment or chemical modification.

In addition to the foregoing materials, the above-described catalysts can be composited with a porous matrix material such as silica, alumina, zirconia, titania, silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia. Mesoporous materials having the MCM-41 or MCM-48 structure may be particularly desirable as supports. The matrix can be in the form of a cogel. A mixture of these components could also be used.

The reaction of the present invention can be conveniently carried out either in batch or continuous operation at from about 20° C. up to about 300° C., preferably between about 50° C. up to about 200° C., and at pressures ranging from about atmospheric pressure up to about 10340 Kpa (1500 psi). Although a batch operation is contemplated, the reaction will preferably be carried out in a continuous mode utilizing various reactor configurations, such as a fixed or packed-bed reactor, in a single or multiple-reactor configuration.

A packed bed provides an effective and efficient reactor. In the packed bed, the reaction zone proceeds along the direction of flow. To minimize the pressure drop across the bed and alleviate potential plugging by debris, the reactor can be operated with the bed expanded by greater than 5%. The reactor also can be operated at conditions for an ebullient bed, a fluidizing bed, or a spouting bed. The use of filters or guard beds may also prevent plugging of the catalyst bed.

In one embodiment of the present invention the formaldehyde-acetal is formaldehyde dimethyl acetal (dimethoxy methane or methylal) and the resulting organic carbonate is dimethyl carbonate.

Although the dimethoxy methane can be provided from various sources, dimethoxy methane can also be produced by reacting methanol with formaldehyde. This reaction can be represented by the following:

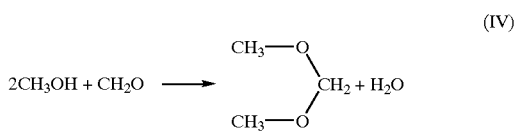

(IV)

The formulation of dimethoxy methane from methanol and formaldehyde is a well-known acid-catalyzed reaction limited by thermodynamic equilibrium, with low temperature favoring the products dimethoxy methane and water. Catalysts, such as organic acids, ion-exchange resins, or porous crystalline aluminosilicates can be used. The reaction can be carried out in either the liquid or gas phase at temperatures less than 200° C., preferably less than 150° C. Stoichiometric amounts of methanol and formaldehyde are used, although an excess of methanol is preferred to minimize side reactions.

When dimethoxy methane is prepared by reacting methanol with formaldehyde in the presence of a catalyst, the dimethoxy methane can be selectively withdrawn as a product or used as a reactant for preparing dimethyl carbonate.

The oxidation reaction of dimethoxy methane to produce dimethyl carbonate can be carried out in a single-reactor fixed bed system. In such a single-reactor system, a source of oxygen is typically passed along with dimethoxy methane over a solid catalyst. The amount of oxygen present in the reaction zone is preferably about a stoichiometric amount or less, relative to the dimethoxy methane, based upon formula (III). The relative concentration of oxygen, which can be in the gas or liquid phase, has to be optimized to achieve high-reaction selectivity to the desired dimethyl carbonate product. Preferably, the source of oxygen is air and the solid catalyst is a metal compound supported on an inert solid matrix, such as, for example, copper compounds on a zeolite support.

The temperature in the reaction zone is from about 20° C. to 300° C., and preferably from about 50° C. to 200° C. In the preferred mode of operation, the reactor temperature is optimized to insure a relatively high conversion and selectivity to dimethyl carbonate.

The products from the oxidation reaction of this invention are recovered and can be separated by distillation, azeotropic distillation, extraction or other techniques well known in the art.

In another embodiment, the oxidation reaction of dimethoxy methane is carried out in a multiple-reactor fixed bed system. In this multiple-reactor system, the fixed-bed reactors undergo alternate reducing and oxidizing environments, for reaction and regeneration, respectively. The cycle length depends on operating conditions, plant design, and the catalytic system to be used. This multiple-reactor system approach allows for better control of the reaction selectivity to the desired dimethyl carbonate and permits the catalyst to be regenerated in a continuous manner. The method of regeneration depends on the particular catalyst used and can include any technique well known in the art.

A fluid-bed process can also be used to perform the oxidation of dimethoxy methane to dimethyl carbonate. The fluid-bed process permits removal and make-up of fresh catalyst, thus, keeping reactor performance constant over a long period of time.

The examples set forth below are for the purpose of illustration and to describe embodiments of the best mode of the invention at the present time. The scope of the invention is not in any way limited by the examples set forth below.

EXAMPLES

The following examples have been carried out to illustrate preferred embodiments of the invention. These examples include the synthesis of dimethoxy methane, the preparation of an oxidizing catalyst system and the synthesis of dimethyl carbonate from dimethoxy methane, utilizing the oxidizing catalyst system.

Examples 1 and 2

Dimethoxy methane was prepared by reacting methanol and trioxane (a cyclic trimer of formaldehyde), in the presence of a zeolite Beta/ZrO$_2$ catalyst in a fixed-bed down-flow reactor. A methanol/trioxane liquid mixture, methanol:trioxane molar ratio of 30:1, was passed over the catalyst using a high-pressure pump. Products were analyzed by on-line gas chromatography. The experiments were performed at 100° C. and 100 psig total pressure. Flow rates of the methanol-trioxane mixture feed, expressed as weight hourly space velocity (WHSV), expressed as grams of methanol-trioxane mixture feed per gram of catalyst per hour, are indicated in Table 1.

TABLE 1

Product Distribution of Reaction of Methanol and Trioxane in Presence of Zeolite Beta/ZrO$_2$ Catalyst
PRODUCTION DISTRIBUTION, WT %

| Ex | WHSV | Dimethoxy Methane | Methanol | Trioxane | Dimethyl Ether |
|---|---|---|---|---|---|
| 1 | 1.4 | 22.9 | 76.9 | 0.0 | 0.2 |
| 2 | 4.9 | 9.2 | 85.6 | 5.2 | 0.0 |

Table 1 illustrates the products produced when a feed stream of methanol and trioxane, containing a molar ratio of 30:1 (methanol:trioxane), was fed to a fixed-bed down-flow reactor containing a Zeolite Beta/ZrO$_2$ catalyst at 100° C. and 100 psig total pressure.

When the feed stream was delivered at a flow rate of 1.4 grams of feed/gram of catalyst per hour in example 1, there was complete conversion of trioxane with a high selectivity to dimethoxy methane and a small amount of dimethyl ether. There was methanol present in the product stream because the feed stream contained excess methanol.

In example 2, the velocity was increased and the conversion decreased. This shows that a sufficient residence time is required to permit the reaction to occur.

Examples 3 & 4

A ruthenium-based catalytic system providing both a source of oxygen and a catalyst as contemplated by the invention was prepared by charging 3 parts of a 0.3 wt % ruthenium tetrachloride aqueous solution in a container, followed by the addition of 2 parts of carbon tetrachloride (CCl$_4$), 2 parts of acetonitrile (CH$_3$CN), and 2 parts of sodium periodate (NaIO$_4$). The resulting mixture was continuously stirred.

Dimethyl carbonate was produced by the oxidation of dimethoxy methane in the presence of the ruthenium-based catalyst. The experiment was carried out as follows: 1 part of dimethoxy methane was charged to a reactor, followed by 70 parts of the mixture, discussed above. The reaction was performed under vigorous stirring at atmospheric pressure and reflux conditions, at approximately 60° C. Liquid reaction products were analyzed by gas chromatography. The results are shown in Table 2.

TABLE 2

Product Distribution of Oxidation Reaction of Dimethoxy Methane
PRODUCT DISTRIBUTION, WT %

| Ex. | Reaction Time Hrs. | Dimethoxy Methane | Dimethyl Carbonate | Hemiacetal | Methanol |
|---|---|---|---|---|---|
| 3 | 1 | 78.3 | 16.7 | 5.0 | Traces |
| 4 | 2 | 53.1 | 32.5 | 14.0 | Traces |

Table 2 illustrates the product distribution of the oxidation reaction of dimethoxy methane charged to a batch reactor with the catalyst/oxygen mixture. The reactor was maintained at 60° C. and atmospheric pressure under reflux conditions.

After two hours a significant amount of dimethyl carbonate was produced, along with some hemiacetal and traces of methanol.

Thus, while there has been disclosed what is presently believed to be the preferred embodiments of the present invention, those skilled in the art will appreciate that other and further changes and modifications can be made without departing from the scope or spirit of the invention, and it is intended that all such other changes and modifications are included in and are within the scope of the invention as described in the appended claims.

What we claim is:

1. A process for preparing an organic carbonate comprising reacting a formaldehyde-acetal with a source of oxygen in the presence of a catalyst.

2. The process of claim 1, wherein said organic carbonate is of the formula:

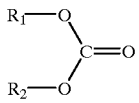

and said formaldehyde-acetal is of the formula:

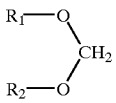

wherein $R_1$ and $R_2$ independently of one another denote a $C_1$–$C_{10}$ linear or branched, substituted or unsubstituted, alkyl radical; a $C_5$–$C_8$ substituted or unsubstituted cycloalkyl radical; or a substituted or unsubstituted $C_6$–$C_{12}$ aryl radical.

3. The process of claim 2, wherein said organic carbonate further comprises dimethyl carbonate and said formaldehyde-acetal further comprises dimethoxy methane.

4. The process of claim 1, wherein said source of oxygen is a reagent selected from the group consisting of $O_2$, air, oxygenated organic compounds; oxygenated inorganic compounds; organic oxides, dioxides and peroxides, inorganic oxides, dioxides and peroxides; periodates; and mixtures thereof.

5. The process of claim 4, wherein said reagent is present with an inert gas or liquid.

6. The process of claim 2, further comprising a secondary process for preparing dimethoxy methane, wherein said secondary process comprises reacting methanol with formaldehyde in the presence of a catalyst and selectively withdrawing said dimethoxy methane as a product for use as the formaldehyde-acetal for preparing said organic carbonate.

7. The process of claim 1, wherein said catalyst comprises a solid support selected from the group consisting of alumina, silica, phosphate, zeolite and mixtures thereof, in which metals, compounds or complexes of an element of groups Ib, VI b, and VIII of the periodic table are incorporated into said support.

8. The process of claim 7, wherein said element of groups Ib, VI b and VIII of the periodic table is present in the form of a metal salt.

9. The process of claim 1, wherein the reaction is carried out in a fixed bed flow reactor.

10. The process of claim 9, wherein the reaction occurs at a temperature in the range from about 20° C. to 300° C. and at a total system pressure of from about atmospheric to about 10340 kPa (1500 psi).

* * * * *